(12) United States Patent
Davies et al.

(10) Patent No.: US 8,735,169 B2
(45) Date of Patent: May 27, 2014

(54) METHODS FOR ANALYZING AGRICULTURAL AND ENVIRONMENTAL SAMPLES

(75) Inventors: Mark Davies, Limerick (IE); Tara Dalton, Patrickswell (IE)

(73) Assignee: Stokes Bio Limited, Limerick (IE)

( * ) Notice: Subject to any disclaimer, the term of this patent is extended or adjusted under 35 U.S.C. 154(b) by 908 days.

(21) Appl. No.: 12/469,339

(22) Filed: May 20, 2009

(65) Prior Publication Data

US 2010/0216128 A1 Aug. 26, 2010

Related U.S. Application Data

(63) Continuation-in-part of application No. 12/092,261, filed as application No. PCT/IE2007/000013 on Feb. 7, 2006.

(60) Provisional application No. 60/765,671, filed on Feb. 7, 2006.

(51) Int. Cl.
*G01N 1/10* (2006.01)

(52) U.S. Cl.
USPC .............. 436/180; 436/53; 436/174; 436/89; 422/82; 422/502; 422/503; 435/6.1; 435/6.12

(58) Field of Classification Search
USPC .............. 422/67, 68.1, 81, 82, 500–502, 504, 422/255–257; 436/52, 53, 174, 180, 89; 700/265, 282, 283, 285; 435/6, 6.1, 435/6.12, 6.15, 288.5, 289.1
See application file for complete search history.

(56) References Cited

U.S. PATENT DOCUMENTS

| 7,235,405 | B2 | 6/2007 | Charles et al. | |
|---|---|---|---|---|
| 2003/0182729 | A1 | 10/2003 | Williams | |
| 2004/0022686 | A1* | 2/2004 | Charles et al. | 422/82.08 |
| 2006/0094119 | A1* | 5/2006 | Ismagilov et al. | 436/53 |
| 2007/0275415 | A1* | 11/2007 | Srinivasan et al. | 435/7.4 |
| 2008/0277494 | A1* | 11/2008 | Davies et al. | 239/86 |

FOREIGN PATENT DOCUMENTS

| EP | 1361442 | 7/2006 |
|---|---|---|
| WO | 01/01106 | 4/2001 |
| WO | 2007/091228 | 8/2007 |
| WO | 2010/133963 | 11/2010 |

OTHER PUBLICATIONS

PCT/IE2007/000013, Written Opinion of The Inerrnational Searching Authority, Aug. 16, 2007.
PCT/IB2010/01233, International Search Report mailed on Oct. 22, 2010.
International Search Report from WO 2007/091228, Aug. 16, 2007.

* cited by examiner

*Primary Examiner* — Brian R Gordon

(57) ABSTRACT

The present invention generally relates methods for analyzing agricultural and/or environmental samples using liquid bridges. In certain embodiments, the invention provides a method for analyzing an agricultural sample for a desired trait including obtaining a gene or gene product from an agricultural sample, in which the gene or gene product is in a first fluid; providing a liquid bridge for mixing the gene or gene product with at least one reagent to form a mixed droplet that is wrapped in an immiscible second fluid; and analyzing the mixed droplet to detect a desired trait of the agricultural sample.

33 Claims, 13 Drawing Sheets

Dimensionless plot of dimensionless plug volume, $V^*$, versus slenderness ratio, where $\Lambda^*$ was $V^*$ scaled with $R_2^3$. Results are plotted for $K^*$ values of 1.0, 0.44 and 0.25.

Liquid bridge dispensing at three different values capillary radii ratio, $K^*$. Capillary tip separations are indicated on the images.

$K^* = 0.25$ $K^* = 0.44$ $K^* = 1.0$

Plug volume variation over fourteen measurements for . K*=0.44 Horizontal lines represent the mean volume dispensed. The mean plug volumes were approximately 120 nL and 56 nL with maximum variations ±4.46% of and ±3.53% respectively.

Funicular liquid bridge supported between three capillaries.
The geometry used to investigate stability is shown
superimposed over the original image.

Experimentally determined stability diagram for a purified water funicular liquid bridge in a density matched silicone oil, Bond number: $1.24 \times 10^{-4}$. Vertical error bars indicate the volumetric ratio uncertainty as a result of camera frame rate.

METHODS FOR ANALYZING AGRICULTURAL AND ENVIRONMENTAL SAMPLES

RELATED APPLICATIONS

The present invention is a continuation-in-part of U.S. nonprovisional patent application Ser. No. 12/092,261, filed Apr. 30, 2008, which is a U.S. national phase patent application from PCT international patent application number PCT/IE2007/000013, filed Feb. 7, 2007, which claims priority to U.S. provisional patent application Ser. No. 60/765,671, filed Feb. 6, 2007, each of which is incorporated by reference herein in its entirety.

FIELD OF INVENTION

The present invention generally relates to methods for analyzing agricultural and/or environmental samples using liquid bridges.

BACKGROUND

In plant development, selective breeding or genetic manipulation are used to make genetic improvements in plants. After a desirable improvement is achieved, commercial quantities are produced by planting and harvesting seeds over several generations. Breeding for enhanced agricultural products involves analysis of a large number of samples from plants to identify those plants with the desired properties for use or advancement to the next generation. For example, analysis of bulk seed batches for certain traits, such as high oil content or protein content, on a single plant or ear, in conjunction with an appropriate breeding methodology such as recurrent selection, often allows for the selection and introduction of such traits into a commercial population. Although the analysis of these seed batches can be performed by various techniques, methods that are rapid and low cost are most desirable.

As agricultural companies continue to introduce a variety of traits into agricultural crops that provide unique compositions and increasing value to the grain and/or its downstream products, there is an increasing need for more sophisticated analysis systems and methods for detecting the traits throughout the value chain, i.e., research and development, seed production, grain production, and grain processing.

SUMMARY

The present invention provides methods and devices for improved agricultural analysis and selective plant breeding. In general, the invention involves using liquid bridges to analyze agricultural and/or environmental samples. Liquid bridges are used to produce sample droplets that contain reaction components for rapid analysis of small sample volumes. Liquid bridges allow the formation of sample droplets by through the interaction of immiscible fluids.

In a preferred embodiment, liquid bridges are used for high throughput analysis of single seeds, allowing for the analysis and identification of agricultural traits in individual seeds or plant extracts. The invention provides significant improvements in the accuracy, speed and resolution of traits in agricultural samples.

An aspect of the invention provides methods for analyzing agricultural samples. In a preferred embodiment, the invention is used to analyze genetic traits in agricultural samples, such as seeds, leaf punches, and the like. An agricultural sample preparation is mixed in a first fluid. The first fluid is placed in a fluidic channel that terminates in a chamber housing a second fluid that is immiscible with the first fluid. Reagents are introduced via another fluidic channel. As droplets containing sample and reagents converge on the chamber, a mixed droplet is formed that contains the sample and reagents wrapped in the immiscible fluid. The droplet can then exit via an exit channel for analysis. Analysis can occur in the channel or in a separate chamber or device.

An exemplary immiscible second fluid is oil. The agricultural sample can be a seed, a batch of seeds, a portion of a seed, or a seed scraping. The agricultural sample can also include plant tissue, such as a leaf, a leaf punch, a flower, a root, and a petal. In certain embodiments, the agricultural sample includes non-plant based material, such as a fungal sample.

The desired trait to be analyzed can be a biochemical trait. Exemplary biochemical traits include oil content, protein content, carbohydrate content, starch content, fiber content, water content, amino acid content, fatty acid content, nitrogen content, chlorophyll fluorescence, metabolites, oil composition, protein composition, carbohydrate composition, and fiber composition. The desired trait can be linked to a genetic marker.

Reagents used to detect a desired trait are selected according to knowledge in the art to support the assay being performed. For example, selected reagents can be a labeled antibody, a nucleic acid probe, a prime, a polymerase, a buffer, etc., and mixtures necessary to carry out a specified reaction or set of reactions.

Another aspect of the invention provides methods for determining traits in a progeny agricultural sample. Nucleic acid from a progeny agricultural sample in a first fluid is introduced into a liquid bridge for mixing with at least one reagent to form a mixed droplet that is wrapped in an immiscible second fluid. Nucleic acid is isolated in respective droplets for analysis. Analysis can take any desired form, such as hybrid capture, PCR, single base extension, and others.

Another aspect of the invention provides a method for analyzing an environmental sample for presence of a biological agent including, providing a liquid bridge for mixing an aliquot of an environmental sample in a first fluid with at least one reagent to form a mixed droplet that is wrapped in an immiscible second fluid, and analyzing the mixed droplet to detect presence or absence of a biological agent in the environmental sample. The method can further include, prior to the providing step, obtaining a gene or gene product from the biological agent in the environmental sample. The method can further include, prior to the analyzing step, performing PCR on the gene from the biological agent in the mixed droplet.

Exemplary environmental samples include a water sample or a soil sample. A biological agent include all genuses and species of bacteria and fungi, including, for example, all spherical, rod-shaped and spiral bacteria. Exemplary bacteria are stapylococci (e.g., *Staphylococcus epidermidis* and *Staphylococcus aureus*), *Enterrococcus faecalis, Pseudomonas aeruginosa, Escherichia coli*, other gram-positive bacteria, and gram-negative bacilli. An exemplary fungus is *Candida albicans*. A biological agent also includes toxins secreted by bacteria or fungi. For example, *E. coli* secretes Shiga-like toxin (Zhao et al., Antimicrobial Agents and Chemotherapy, 1522-1528, 2002) and *C. Difficile* secretes Exotoxin B (Sifferta et al. Microbes & Infection, 1159-1162, 1999). A biological agent can also include an allergen. An allergen is a nonparasitic antigen capable of stimulating an immune response in a subject. Allergens can include plant pollen or dust mite excretion.

DETAILED DESCRIPTION

Figure 1A:
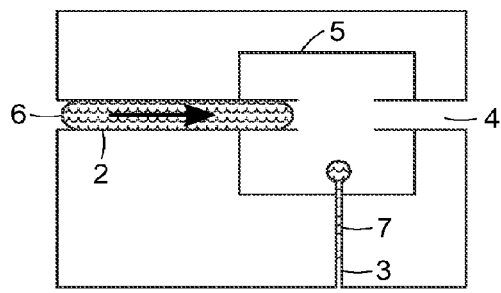
FIG. 1 is a drawing depicting an exemplary embodiment of a liquid bridge having two inlets and one outlet.
Figure 1B:
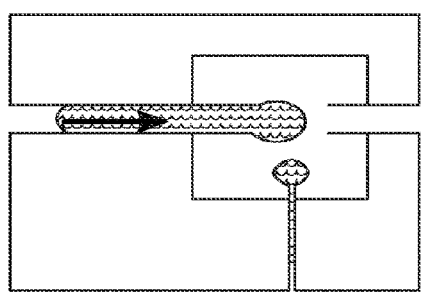
Figure 1C:
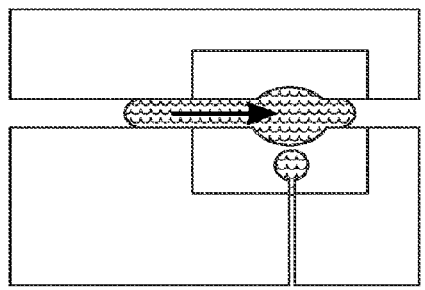
Figure 1D:
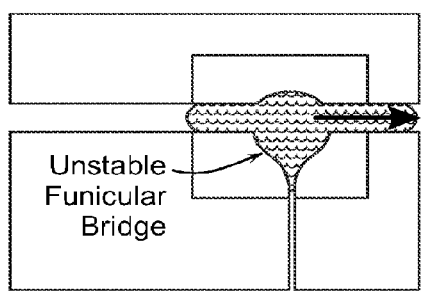
Figure 1E:
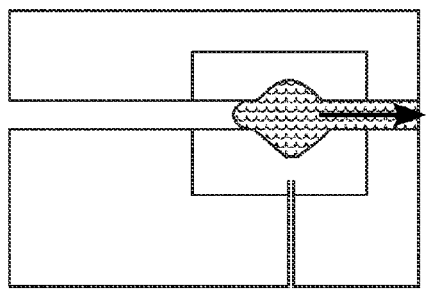
Figure 1F:
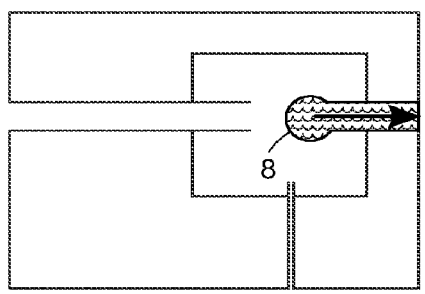
Figure 1G:
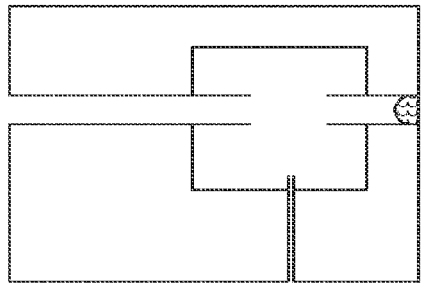
Figure 2A:
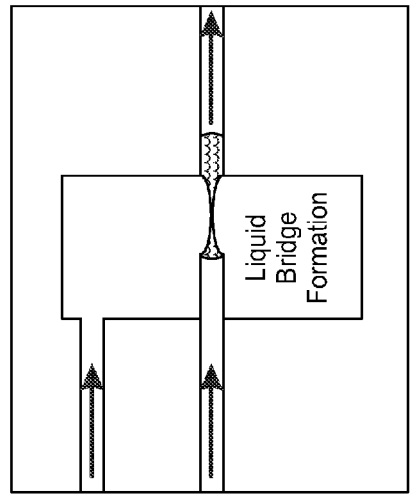
FIG. 2 is a drawing depicting another exemplary embodiment of a liquid bridge having two inlets and one outlet.
Figure 2B:
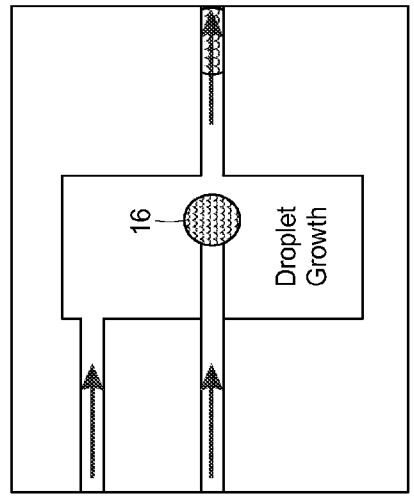
Figure 2C:
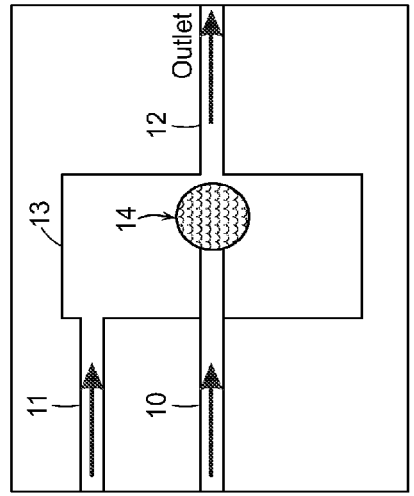
Figure 2D:
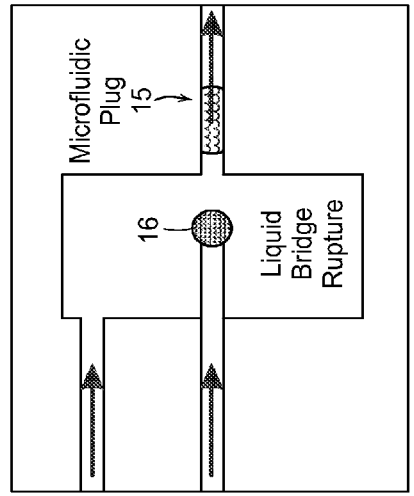
Figure 3A:
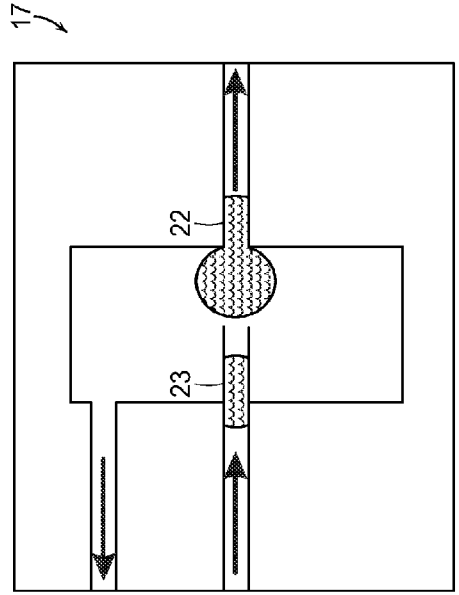
FIG. 3 is a drawing depicting an exemplary embodiment of a liquid bridge having one inlet and two outlets.
Figure 3B:
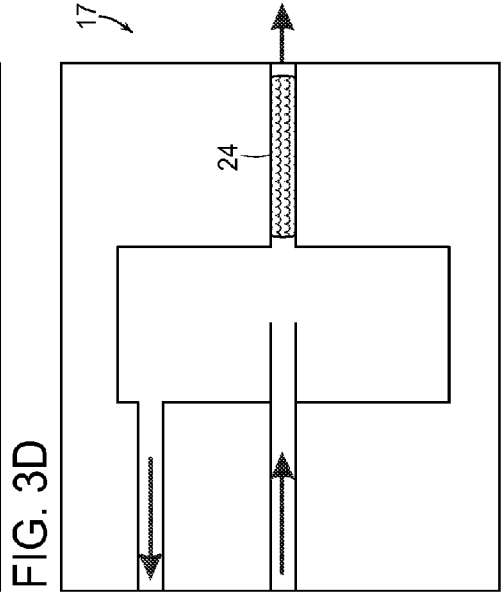
Figure 3C:
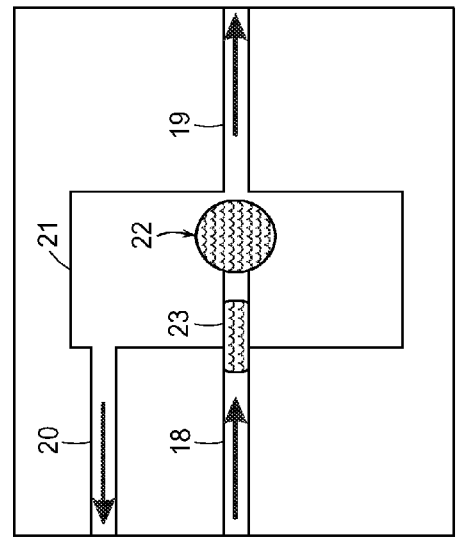
Figure 3D:
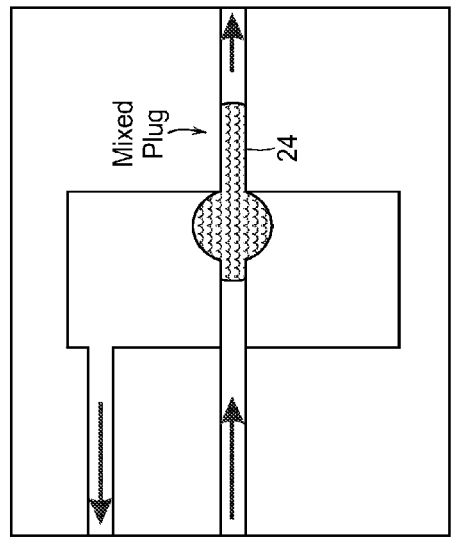

The present invention generally relates to methods for analyzing agricultural and/or environmental samples using liquid bridges. An aspect of the invention provides a method for analyzing an agricultural sample for a desired trait. An agricultural sample includes any plant material that is being interrogated by a method of the present invention. An agricultural sample includes, but is not limited to, seeds or plant tissue. Seeds include a single seed, a batch of seeds, a portion of a seed, or a seed scraping. The seed can be any type of seed, such as alfalfa seed, apple seed, banana seed, barley seed, bean seed, broccoli seed, castorbean seed, citrus seed, clover seed, coconut seed, coffee seed, maize seed, cotton seed, cucumber seed, Douglas fir seed, Eucalyptus seed, Loblolly pine seed, linseed seed, melon seed, oat seed, olive seed, palm seed, pea seed, peanut seed, pepper seed, poplar seed, Radiata pine seed, rapeseed seed, rice seed, rye seed, sorghum seed, Southern pine seed, soybean seed, strawberry seed, sugarbeet seed, sugarcane seed, sunflower seed, sweetgum seed, tea seed, tobacco seed, tomato seed, turf, wheat seed, and *Arabidopsis thaliana* seed.

Plant tissue includes, but is not limited to, any plant part such as leaf, flower, root, or petal. Plant tissue can also include a leaf punch. The plant tissue can by from any plant, such as alfalfa, barley, canola, corn, cotton, oats, potato, rice, rye, soybean, sugarbeet, sunflower, sorghum, and wheat. An agricultural sample also includes non-plant based material such as non-organic matter or non-plant based matter that occurs in an agricultural context. Fungal samples are also examples of an agricultural sample.

Methods of the invention involve obtaining a sample comprising a gene, gene product, or other marker from an agricultural sample. Methods of obtaining genes and/or gene products from agricultural samples are well known in the art. DNA may be extracted from the agricultural sample using any DNA extraction methods known to those of skill in the art that will provide sufficient DNA yield, and DNA quality. A non-limiting example of suitable DNA-extraction methods is SDS-based extraction with centrifugation. Bhat et al. (U.S. Pat. No. 7,208,654, the contents of which are incorporated by reference herein in their entirety) provides another exemplary method for extracting DNA from an agricultural sample. Briefly, to extract DNA, REDExtract-N-Amp Plant PCR kit (Cat # XNA-P, Sigma, 3050 Spruce Street, St. Louis, Mo. 63103 USA) can be used. DNA is extracted as follows: 100 μl of Extraction Solution is added to a vessel containing a leaf punch and the vessel is covered with a plate sealer. The vessel is heated to 95° C. for 10 minutes in a heat block. The vessel is then cooled to room temperature and then again heated at 95° C. for 10 minutes. The vessel is cooled to room temperature and then spun in a microfuge before removing the sealer. To each well an equal amount of Dilution buffer is added (provided in the kit).

The sample can be introduced into the liquid bridge "in situ", that is without preparation. However, in many embodiments, it is desirable to process the sample prior to isolating the analyte to be detected. For example, the agricultural sample can be crushed, pulverized, ground, cut, punched, scraped, etc. Methods for manipulating agricultural samples are well known in the art. See, for example, Bhat et al. (U.S. Pat. No. 7,208,654), Deppermann et al. (U.S. Pat. No. 7,502,113), Armstrong et al. (U.S. Pat. No. 6,603,061), Feng et al. (U.S. Pat. No. 6,107,549), Frayley et al. (U.S. Pat. No. 6,255,560), Kotyk et al. (U.S. Pat. No. 7,367,155), Modiano et al. (U.S. Pat. No. 6,646,264), Modiano et al. (US 2007/0240242), and Das et al. (US 2009/0075325), the contents of each of which is incorporated by reference herein in their entirety. In certain embodiments, the gene or gene product is obtained from a seed scraping. Seed scraping can be performed manually or by using a machine. Methods and systems for obtaining a seed scraping are shown in Deppermann et al. (U.S. Pat. No. 7,502,113).

Methods of the invention further include providing a liquid bridge for mixing the gene or gene product with at least one reagent to form a mixed droplet that is wrapped in an immiscible carrier fluid. Exemplary liquid bridges are shown in Davies et al. (WO 2007/091228, the contents of which are incorporated by reference herein in their entirety). In certain embodiments, a liquid bridge includes a chamber having at least one inlet and at least one outlet. The chamber can include as many inlets and outlets as are desired, for example, one inlet and one outlet, two inlets and two outlets, three inlets and three outlets, four inlets and four outlets, one inlet and two outlets, one inlet and three outlets, one inlet and four outlets, two inlets and one outlet, etc.

The liquid bridge chamber and its inlets and outlets can be composed of any inert material that does not interact with the sample or the carrier fluid. Exemplary materials include polytetrafluoroethylene (PTFE; commercially available from Dupont, Wilmington, Del.), polyetheretherketone (PEEK; commercially available from TexLoc, Fort Worth, Tex.), perfluoroalkoxy (PFA; commercially available from TexLoc, Fort Worth, Tex.), or Fluorinated ethylene propylene (FEP; commercially available from TexLoc, Fort Worth, Tex.).

The chamber is configured to receive a carrier fluid, the carrier fluid filling a space in the chamber between the inlet and the outlet. The carrier fluid is immiscible with the sample. In embodiments in which the sample is hydrophilic, an exemplary carrier fluid is an oil, for example silicone oil. In certain embodiments, the silicone oil is PD5 oil. In other embodiments, the oil is any oil that contains a phenol group. Alternatively, the sample can be hydrophobic and exemplary carrier fluids include water or alcohol such as methanol or ethanol.

In certain embodiments, the carrier fluid is density matched with the sample such that a neutrally buoyant environment is produced within the chamber. In embodiments in which the carrier fluid is an oil, the oil typically provides a pressure of no more than 0.5 to 1.0 bar above atmospheric pressure. The oil generally has a viscosity of about 0.08 Pas to about 0.1 Pas.

The inlets and outlets can be of any shape, for example, circular, rectangular, triangular, or square. The inlets and outlets can have an inner diameter ranging from about 10 μm to about 3 mm. For example, the inlets an outlets have an inner diameter of about 10 μm, about 50 μm, about 100 μm, about 150 μm, about 200 μm, about 400 μm, about 600 μm, about 900 μm, about 1 mm, about 2 mm, or about 3 mm. In certain embodiments, the inlets and outlets have the same inner diameter. In other embodiments, the inlets and outlets have different inner diameters. In certain embodiments, each of the inlets have different inner diameters. In certain embodiments, each of the outlets have different inner diameters.

The inlet(s) and outlet(s) have dimensions and are positioned in the chamber such that a sample periodically bridges from the inlet(s) to the outlet(s), and droplets of the sample are periodically delivered to the outlet(s). FIG. 1 shows an exemplary embodiment of a liquid bridge having two inlets and one outlet. Referring to FIG. 1 panel A, a bridge 1 includes a first inlet 2, a narrower second inlet 3, an outlet 4, and a chamber 5. The chamber is filled with a carrier fluid, e.g., silicone oil, and the carrier fluid is density-matched with the first sample 6 such that a neutrally buoyant environment is created within the chamber 5. The oil within the chamber is continuously replenished by the oil separating formed droplets of sample. Replenishment of the oil separating the formed droplets results in the droplets assuming a stable capillary-suspended spherical form upon entering the chamber 5.

FIG. 1 panels B and C show that the spherical shape of the sample grows until large enough to span the gap between the ports, forming an axisymmetric liquid bridge. FIG. 1 panel D shows that introduction of a second sample droplet 7 from the second inlet 3 results in formation of an unstable funicular bridge. FIG. 1 panel E shows that the unstable funicular bridge quickly ruptures from the second inlet 3, and the first and second sample droplets combine at the liquid bridge 1. FIG. 1 panels F and G show that upon combination with the first sample 6 and the second sample 7, the droplet 8 containing each of the first sample 6 and the second sample 7 ruptures from the first inlet 2 and enters the outlet 4.

In further detail, the first inlet 2 and the outlet 3 are of diameter 200 μm. The separation of the inlet 2 and the outlet 4 is about 1 mm. The second inlet 3 is of diameter 100 μm, and the distance between the second inlet 3 and the axis of the inlet 2 and the outlet 4 is 1.5 mm. The chamber 5 is 5 mm in diameter and 3 mm in depth. The carrier fluid, e.g., oil provides a pressure of no more than 0.5 to 1.0 bar above atmospheric, and has a viscosity of 0.08 to 0.1 Pas. The flow rate of the samples 6 and 7 entering chamber 5 is in the range of 2 μl/min to 5 μl/min. The carrier fluid is density-matched with each of samples 6 and 7 such that a neutrally buoyant environment is created within the chamber 5.

The pressure in the chamber 5 is atmospheric. The interfacial tension within the chamber 5 is important for effective mixing of samples 6 and 7. Also, the relative viscosity between the samples and carrier fluid is important. The internal pressure (Laplace pressure) within each droplet is inversely proportional to the droplet radius. Thus there is a higher internal pressure within the droplet at the second inlet 3. Because sample 6 and sample 7 are of the same phase, there is little interfacial tension between the droplets of these fluids. Thus, the internal pressures cause a joining of the droplets, akin to injection of one into the other. Also, physical control of the locations of the sample droplets 6 and 7 is achieved by the carrier fluid, which is immiscible with the droplets. In certain embodiments, a surfactant can be added to either the samples 6 and 7 or the carrier fluid to change the interfacial tension.

FIG. 2 shows another exemplary embodiment of a liquid bridge having two inlets and one outlet. Referring to FIG. 2 panel A, liquid bridge 9 includes a first inlet 10, a second inlet 11, an outlet 12, and a chamber 13. The chamber 13 is filled with a carrier fluid, e.g., silicone oil. The chamber 13 is 5 mm in diameter and 3 mm in depth, and the internal pressure caused by flow of carrier fluid, e.g., silicone oil, from the second inlet 11 into the chamber 13 is no more than 0.5 bar to 1.0 bar above atmospheric pressure. The diameter of the inlets 10 and 11 and outlet 12 is 200 μm. The spacing between the first inlet 10 and the outlet 12 is 0.5 mm. The spacing between these ports can range from 0.2 mm to 1.5 mm. The flow rate of the sample from the inlet 10 into the chamber 13 is 5 μl/min. The flow rate can generally range from about 2 μl/min to about 8 μl/min.

The geometry between liquid bridge 9, and the carrier fluid create a periodic instability between the inlet 10 and the outlet 12 due to surface tension. FIG. 2 panel A shows that an sample droplet 14 is initially formed at the end of the inlet 10. As shown in FIG. 2 panel B, the sample droplet 14 momentarily bridges between the inlet 10 and the outlet 12. The volume held in this bridge is then steadily reduced by the action of pumping carrier fluid into the chamber through the second inlet port 11. FIG. 2, panels B and C show that pumping carrier fluid into the chamber while the sample droplet 14 momentarily bridges between the inlet port 10 and the outlet port 12 results in the formation of an unstable liquid bridge that ruptures to release a microfluidic plug 15 of sample that enters the outlet 12. FIG. 2 panel D shows that subsequent to rupture of the microfluidic plug 15, the process repeats itself with the formation of another sample droplet 16 at the end of inlet 10.

When the flow rate of the carrier fluid entering the chamber 13 from inlet port 12 is substantially the same as the flow rate of sample entering the chamber 13 from the inlet port 10, smaller segmented droplets, separated by the same volume of carrier fluid, e.g., silicone oil, are produced by the bridge 9. The segmenting mechanism reliably produces uniform aqueous microfluidic plugs separated by carrier fluid that do not rely on the shear force exerted by the carrier fluid.

In another embodiment, mixing of sample droplets may be achieved using a configuration in which a chamber includes one inlet and two outlets. Sample droplets entering the chamber through the inlet are close together, and the delay for droplet formation within the chamber due to a reduction in fluid flow through a main line results in a collision and hence mixing. Such mixing may be caused by withdrawal of oil from the chamber, or upstream of it. Referring to FIG. 3, a liquid bridge 17 has an inlet 18, a first outlet 19, a second outlet 20, and a chamber 21. The chamber is filled with carrier fluid, e.g., oil, that is immiscible with the sample. A leading droplet of sample entering the chamber 21 through the inlet 18 forms a sample droplet 22 in the chamber at the end of the inlet 18. FIG. 3 panels B and C show that as carrier fluid, e.g., oil, is withdrawn from the chamber 21 through the second outlet 20, a smaller trailing sample droplet 23 collides with the leading sample droplet 22 so that the mixing occurs. FIG.

3 panel D shows a larger mixed sample droplet 24 leaving the chamber 21 via the first outlet 19.

In more detail, initially, the entire system is primed with a density matched carrier fluid, e.g., oil. The diameter of the inlet 18 and the outlets 19 and 20 is 250 μm. The spacing between the inlet 18 and the outlet 19 is about 1 mm. The spacing between the inlet and outlet can range from 0.2 mm to 1.5 mm. The carrier fluid is controlled to have a pressure of about 0.5 bar to about 1.0 bar above atmospheric. The carrier fluid, e.g., silicone oil, has a viscosity of 0.08 to 0.1 Pas.

As with liquid bridges 1 and 9, sample droplets are enveloped by carrier fluid entering and exiting the bridge 17 via a protective film of the carrier fluid firm around the sample droplets. This provides a non-contacting solid surface that prevents carryover contamination from one sample droplet to the next sample droplet. The carrier fluid is used as the control fluid and is density-matched with the sample plugs such that a neutrally buoyant environment is created within the chamber. When two unmixed sample droplets arrive at the chamber in series from the inlet 18, the first droplet assumes a stable capillary-suspended spherical form upon entering the chamber (FIG. 3, panel A). The spherical shape grows until large enough to span the gap between the ports, forming an axisymmetric liquid bridge (FIG. 3, panel B). The second outlet 20 removes a flow of carrier fluid, e.g., oil, from the chamber causing the first sample droplet to slow and remain as a spherical shape at the first outlet 19. This allows time for a second sample droplet to form a stable capillary-suspended spherical shape on entering the chamber 21. With the first sample droplet formed as a spherical shape at the outlet 19, and the second droplet formed as a spherical shape at the inlet 18, the first and second sample droplets can form as one and create an axisymmetric liquid bridge (FIG. 3, panel C). The mixed droplet then exits through the outlet port 19 (FIG. 3, panel D).

In certain embodiments, the flow conditions should be adjusted such that flow through the inlet 18 is greater than the flow through the second outlet 20. A typical flow through the inlet port 18 is about 5 μl/min, and can generally range from about 2 μl/min to about 7 μl/min. The flow away from the chamber 21 through the second outlet 20 is typically 2.5 μl/min and can generally range from about 1 μl/min to about 5 μl/min. Since there is conservation of mass flow within the bridge, this means that the flow through the first outlet 19 will balance the bridge to give a flow of typically 2.5 μl/min, and can generally range from about 1 μl/min to about 5 μl/min.

In certain embodiments, the liquid bridge 17 can be used with a constant outlet flow rate through the second outlet 20. In this embodiment, droplets can be mixed and the fluid flow through the system can be decreased. In addition, liquid bridge 17 can be used in conjunction with a sensor to time the withdrawal of fluid through the second outlet 20 so as to maintain a generally constant sample flow rate.

The sensor used can be a droplet detection sensor that includes a LED and photodiode. The LED is projected directly onto the center of the tube. A photodiode is positioned directly opposite the LED to pick up the light refracted through the rube. As a sample droplet having varying properties compared to that of the carrier fluid, e.g., oil, flows past the LED and photodiode, the light refracted through the liquid is altered slightly. This slight alteration is detected by the photodiode in the form of a change in voltage. This change in voltage can be used to time the control flow through second outlet port 20.

Liquid bridge systems of the invention can further include at least one robotics system to control the gas-free sampling devices. The robotics systems control movement of the sampling device between wells of the first and second arrays and also control sample acquisition. At least one pump is connected to the sampling device. An exemplary pump is shown in Davies et al. (WO 2007/091229, the contents of which are incorporated by reference herein in their entirety). Other commercially available pumps can also be used. The pumps are controlled by a flow controller, e.g., a PC running WinPumpControl software (Open Cage Software, Inc., Huntington, N.Y.), for control of direction of flow and flow rates.

Liquid bridge systems can be fluidly connected, e.g., tubes or channels, to an type of analysis device. In certain embodiments, the liquid bridge system is connected to a thermocycler to perform PCR reactions on the acquired sample. An exemplary thermocycler and methods of fluidly connecting a thermocycler to a liquid bridge system are shown in Davies et al. (WO 2005/023427, WO 2007/091230, and WO 2008/038259, the contents of each of which is incorporated by reference herein in its entirety). The thermocycler can be connected to an optical detecting device to detect the products of the PCR reaction. An optical detecting device and methods for connecting the device to the thermocycler are shown in Davies et al. (WO 2007/091230 and WO 2008/038259, the contents of each of which is incorporated by reference herein in its entirety).

In certain embodiments, the system is configured to perform single molecule detection, including digital PCR. Liquid bridge systems of the invention are useful in application in which one desires to detect and/or analyze a small number of analytes, down to the single molecule level. For example, the invention is useful for the detection of a desired analyte (e.g., a protein, a nucleic acid, a carbohydrate, or other biomarkers) in a heterogeneous sample. One important application of single molecule detection is digital nucleic acid amplification. Digital amplification and digital PCR are shown in Davies et al. (WO 2007/091230). Digital amplification is the process in which one amplifies a single nucleic acid template in order to generate a clonal population of amplicons. Digital amplification is useful to identify template molecules in samples, such as complex heterogeneous samples (e.g., urine, sputum, stool, puss, blood, or other bodily fluids); or to monitor a PCR reaction.

Digital PCR uses use fluorescent probes to monitor the amplification process as it progresses. SYBR Green 1 dye is an exemplary dye used for fluorescent detection of double-stranded DNA generated during PCR. Through the analysis of the cycle-to-cycle change in fluorescence signal important information regarding the DNA sample is obtained. This is accomplished by illuminating the sample and detecting the resulting fluorescence. Different product concentration will demonstrate fluorescence amplification at difference cycle numbers. Through the analysis of the behavior of the sample the characterization is possible. An exemplary system for digital PCR is disclosed in Davies et al. (WO 2007/091230).

Methods of the invention further include analyzing the mixed droplet to detect a desired trait of the agricultural sample. The desired trait to be detected can be a biochemical trait, a marker, or a genotype. Exemplary biochemical traits include oil content, protein content, carbohydrate content, starch content, fiber content, water content, amino acid content, fatty acid content, nitrogen content, chlorophyll fluorescence, metabolites, oil composition, protein composition, carbohydrate composition, and fiber composition.

In other embodiments, the desired trait is linked to a genetic marker. In these embodiments, the desired trait is detected by extracting DNA from the agricultural samples, and screening the DNA for the presence or absence of the genetic marker. A wide variety of genetic markers are available and known to those of skill in the art. The screening may be used to select for quantitative trait loci (QTL), alleles, or genomic regions (haplotypes).

In one embodiment, the desired trait is linked to the presence or absence of a genetic marker that is genetically linked with a QTL. Examples of QTLs which are often of interest include but are not limited to yield, lodging resistance, height, maturity, disease resistance, pest resistance, resistance to nutrient deficiency, and grain composition. Alternatively, the desired trait is linked to the presence or absence of a marker that is genetically linked with a haplotype associated with a QTL. Examples of such QTL may again include without limitation yield, lodging resistance, height, maturity, disease resistance, pest resistance, resistance to nutrient deficiency, and grain composition.

Included within selectable or screenable marker genes are also genes that encode a secretable marker whose secretion can be detected as a method of identifying or selecting for transformed cells in an agricultural sample. Examples include markers that encode a secreted antigen that can be identified by antibody interaction, or even secreted enzymes that can be detected catalytically. Secreted proteins fall into a number of classes, including small, diffusible proteins detectable, e.g., by ELISA, small active enzymes detectable in extracellular solution (e.g., α-amylase, β-lactamase, phosphinothricin transferase), or proteins that are inserted or trapped in the cell wall (such as proteins which include a leader sequence such as that found in the expression unit of extension or tobacco PR-S). Other possible selectable and/or screenable marker genes will be apparent to those of skill in the art.

A variety of agents are useful in analyzing and detecting analytes in the sample (e.g., a desired trait). Such agents include, for example, polynucleotides, polypeptides, small molecules, and/or antibodies useful in in situ screening assays for detecting the desired trait. An agent can be detectably labeled such that the agent is detectable when bound or hybridized to its target biomarker or ligand. Detectably labeling any of the foregoing agents includes an enzymatic, fluorescent, or radionucleotide label. Other reporter methods and labels are well known in the art.

An agent useful in the methods of the invention can be an antibody. The term "antibody" as referred to herein includes whole antibodies and any antigen binding fragment (i.e., "antigen-binding portion") or single chains of these. A naturally occurring "antibody" is a glycoprotein including at least two heavy (H) chains and two light (L) chains inter-connected by disulfide bonds.

Antibodies useful in the methods of the invention include intact polyclonal or monoclonal antibodies, as well as fragments thereof, such as Fab and F(ab')$_2$. For example, monoclonal antibodies are made from antigen containing fragments of a protein by methods well known to those skilled in the art (Kohler, et al., Nature, 256:495, 1975; and Harlow et al., Antibodies, Cold Spring Harbor Laboratory, pp. 93-117, 1988). Fluorescent molecules may be bound to an immunoglobulin either directly or indirectly by using an intermediate functional group.

An agent useful in the methods of the invention can also be a nucleic acid molecule (e.g., an oligonucleotide or polynucleotide probe). For example, in situ nucleic acid hybridization techniques are well known in the art and can be used to identify a RNA or DNA biomarker present in an agricultural sample. Screening procedures that rely on nucleic acid hybridization make it possible to identify a biomarker from any sample, provided the appropriate oligonucleotide or polynucleotide agent is available. For example, oligonucleotide agents, which can correspond to a part of a sequence encoding a target polypeptide, can be synthesized chemically or designed through molecular biology techniques. See Sambrook, et al., Molecular Cloning—A Laboratory Manual, Cold Spring Harbor Laboratory, Cold Spring Harbor, N.Y. (1985). The polynucleotide encoding the target polypeptide can be deduced from the genetic code, however, the degeneracy of the code must be taken into account. For such screening, hybridization is typically performed under in situ conditions known to those skilled in the art.

A number of fluorescent labels are known in the art and include DAPI, Cy3, Cy3.5, Cy5, Cy5.5, Cy7, umbelliferone, fluorescein, fluorescein isothiocyanate (FITC), rhodamine, dichlorotriazinylamine fluorescein, dansyl chloride or phycoerythrin. A fluorescent label should have distinguishable excitation and emission spectra. Where two or more fluorescent labels are used, they should have differing excitation and emission spectra that differ, respectively, by some minimal value (typically about 15-30 nm). The degree of difference will typically be determined by the types of filters being used in the process. Typical excitation and emission spectra for DAPI, FITC, Cy3, Cy3.5, Cy5, Cy5.5, and Cy7 are provided below in table 1.

TABLE 1

| Fluorescent indicator | Excitation Peak | Emission Peak |
|---|---|---|
| DAPI | 350 | 450 |
| FITC | 490 | 520 |
| Cy3 | 550 | 570 |
| Cy3.5 | 580 | 595 |
| Cy5 | 650 | 670 |
| Cy5.5 | 680 | 700 |
| Cy7 | 755 | 780 |

In other embodiments, the reagents are PCR reagents. A typical Q-PCR reaction contains: fluorescent double-stranded binding dye, Taq polymerase, deoxynucleotides of type A, C, G, and T, magnesium chloride, forward and reverse primers and cDNA, all suspended within an aqueous buffer. Reactants, however, may be assigned into two broad groups: universal and reaction specific. Universal reactants are those common to every Q-PCR reaction, and include: fluorescent double-stranded binding dye, Taq polymerase, deoxynucleotides A, C, G and T, and magnesium chloride. Reaction specific reactants include the forward and reverse primers and patient cDNA.

Oligonucleotide primers refer to linear, single-stranded, oligomeric deoxyribonucleic or ribonucleic acid molecules capable of sequence-specific hybridization (annealing) with complementary strands of modified or unmodified nucleic acid. In certain embodiments, the specific primers are DNA. The primers of the invention embrace oligonucleotides of appropriate sequence and sufficient length so as to provide for specific and efficient initiation of polymerization (primer extension) during the amplification process. As used in the inventive processes, oligonucleotide primers typically contain 12-30 nucleotides or more, although may contain fewer nucleotides. The exact length will depend on multiple factors including temperature (during amplification), buffer, and nucleotide composition. In certain embodiments, primers are single-stranded although double-stranded primers may be used if the strands are first separated. Primers may be prepared using any suitable method, such as conventional phosphotriester and phosphodiester methods or automated embodiments which are commonly known in the art. The specific primers may be designed to be substantially complementary to each strand of the genomic locus of interest.

Typically, one primer is complementary to the negative (−) strand of the locus (the "lower" strand of a horizontally situated double-stranded DNA molecule) and the other is complementary to the positive (+) strand ("upper" strand).

Analytical methods of the invention allow individual seeds to be analyzed that are present in a batch or a bulk population of seeds such that the chemical and/or genetic traits of the individual seeds can be determined. Exemplary traits include starch content, protein content, oil content, determination of fatty acid profiles, etc.

Methods of the present invention can also be used in a breeding program to select plants or seeds having a desired trait or marker genotype. The methods of the present invention can be used in combination with any breeding methodology and can be used to select a single generation or to select multiple generations. DNA is obtained from the seed and analyzed for the presence or absence of at least one genetic marker. Based on the results of the DNA screening, seeds can be selected from the population, and plants can be cultivated from the selected seed. The choice of breeding method depends on the mode of plant reproduction, the heritability of the trait(s) being improved, and the type of cultivar used commercially (e.g., $F_1$ hybrid cultivar, pureline cultivar, etc). Exemplary traits that can be detected include emergence vigor, vegetative vigor, stress tolerance, disease resistance, branching, flowering, seed set, seed size, seed density, standability, and threshability etc. In a particular embodiment, the methods of the present invention are used to determine the genetic characteristics of seeds in a marker-assisted breeding program.

Methods of the invention may also be used for introgressing a trait into a plant by removing DNA from an agricultural sample, screening the DNA extracted from the sample for the presence or absence of at least one genetic marker, selecting seeds from the population based upon the results of the DNA screening, cultivating a fertile plant from the seed, and utilizing the fertile plant as either a female parent or male parent in a cross with another plant. Examples of genetic screening to select seeds for trait integration include, without limitation, identification of high recurrent parent allele frequencies, tracking of transgenes of interest or screening for the absence of unwanted transgenes, selection of hybrid testing seed, and zygosity testing.

The identification of high recurrent pair allele frequencies via the screening methods of the present invention again allows for a reduced number of rows per population and an increased number of populations, or inbred lines, to be planted in a given field unit. Thus, the screening methods of the present invention may also effectively reduce the resources required to complete the conversion of inbred lines. The methods of the present invention further provide quality assurance and quality control by assuring that regulated or unwanted transgenes are identified and discarded prior to planting.

The methods of the present invention may be further applied to identify hybrid seeds for transgene testing. For example, in a conversion of an inbred line at the $BCnF_1$ stage, a breeder could effectively create a hybrid seed lot (barring gamete selection) that was 50% hemizygous for the trait of interest and 50% homozygous for the lack of the trait in order to generate hybrid seeds for testing. The breeder could then screen all $F_1$ seeds produced in the test cross and identify and select those seeds that were hemizygous. Such a method is advantageous in that inferences from the hybrid trials would represent commercial hybrid genetics with regard to trait zygosity.

In certain embodiments, methods of the invention are used to determine ploidy of an organism. Ploidy refers to the number of complete sets of chromosomes in an organism, such as a plant. Plants can be, for example, haploid, diploid, triploid, tetraploid, polyploid, or aneuploid. Also, ploidy of cells can vary within an organism.

Still further, screening methods of the invention are used to improve the efficiency of a doubled haploid program. In agriculture, a doubled haploid is an organism having two identical sets of chromosomes. Double haploids are produced from haploid pollen or egg cells that are induced to undergo chromosome doubling. Haploid cells occur naturally in the gametophytic phases of higher plants in their ovules and pollen. By manipulating the gametic cells, it is possible to produce homozygous embryos rather than mature pollen grains or ovules. By induced or spontaneous chromosome doubling, a completely homozygous doubled haploid plant can be produced. Conventional inbreeding procedures take about six generations to achieve completely homozygous genomes, whereas double haploidy reduces the breeding process to essentially one step. Using methods of the invention described above, one improve the efficiency of a doubled haploid program through selection of desired genotypes at the haploid stage and identification of ploidy level to eliminate non-haploid seeds from being processed and advancing to the field.

In another embodiment, the invention further provides an assay for predicting embryo zygosity for a particular gene of interest. The assay predicts embryo zygosity based on the ratio of the relative copy numbers of a selected gene and an internal control gene per cell or per genome. Generally, this assay uses a control gene that is of known zygosity, for normalizing measurement of the selected gene. The ratio of the relative copy numbers of the control to the selected gene predicts the gene copy number in the cell. In a homozygous cell, for any given gene (or unique genetic sequence), the gene copy number is equal to the ploidy of the cell since the sequence is present at the same locus in all homologous chromosomes. When a cell is heterozygous for a particular gene, the gene copy number will be lower than the ploidy level of the cell. The zygosity of a cell at any locus can thus be determined by the gene copy number in the cell.

The invention having now been described, it is further illustrated by the following examples and claims, which are illustrative and are not meant to be further limiting. Those skilled in the art will recognize or be able to ascertain using no more than routine experimentation, numerous equivalents to the specific procedures described herein. Such equivalents are within the scope of the present invention and claims.

The contents of all references and citations, including issued patents, published patent applications, and journal articles cited throughout this application, are hereby incorporated by reference in their entireties for all purposes.

EXAMPLES

Example 1

Rupturing of a Sample in a Liquid Bridge

Figures 4A, 4B, 4C:
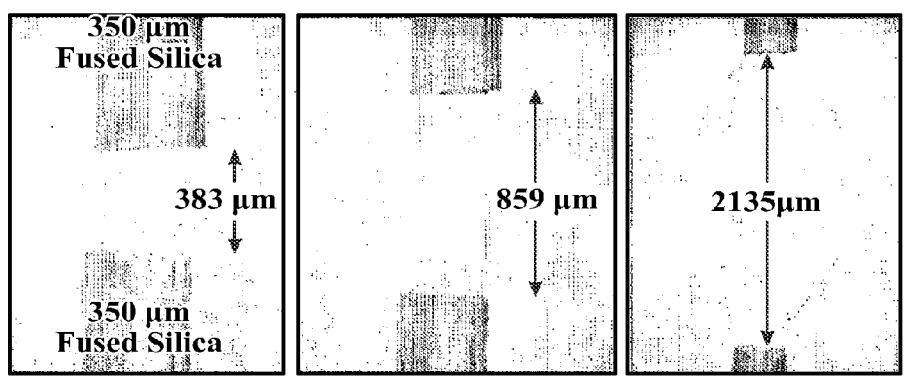
FIG. 4 is a sequence of photographs showing liquid dynamics and dimensions at a liquid bridge.

Liquid bridge stability was studied as a means to predicting the geometric conditions at which rupture occurs. Liquid bridge rupture may be defined as the complete breakage of the liquid filament connecting one solid support to the other. The dimensionless parameters characterizing liquid bridges are used to define the stability boundary at which rupture was observed. FIG. 4 presents images of liquid bridges at three slenderness conditions just prior to rupture. The rupture was caused by the withdrawal of liquid bridge fluid from one capillary tube. It was observed that low slenderness ratio liquid bridges, an example of which is shown in FIG. 4, panel A, adopt a thimble shape at the minimum volume stability. Larger slenderness ratio liquid bridges, such as that shown in FIG. 4, panel C, possess a barrel form with a maximum radius at the bridge mid-span. Intermediate slenderness ratios were found to have a near cylindrical shape at the minimum volume stability limit. FIG. 4, panels A-C show liquid bridges with slenderness ratios of 1.09, 2.45 and 6.16 respectively.

Example 2

Stability of a Liquid Bridge with Respect to Slenderness and Volume

The stability of liquid bridges was examined as a function of slenderness, $\Lambda^*$, which is the ratio of tip separation, L, to the mean diameter, $2R_0$, of the supporting capillaries, i.e. $\Lambda^*=L/2R_0$. Stability was also investigated as a function of volumetric ratio, $V^*$, which is the ratio of liquid bridge volume to the volume of a cylinder with a radius $R_0$, the average radius of the supporting capillaries, i.e.:

$$V^*=\overline{V}/(\pi R_0^3 L).$$

Figure 7:
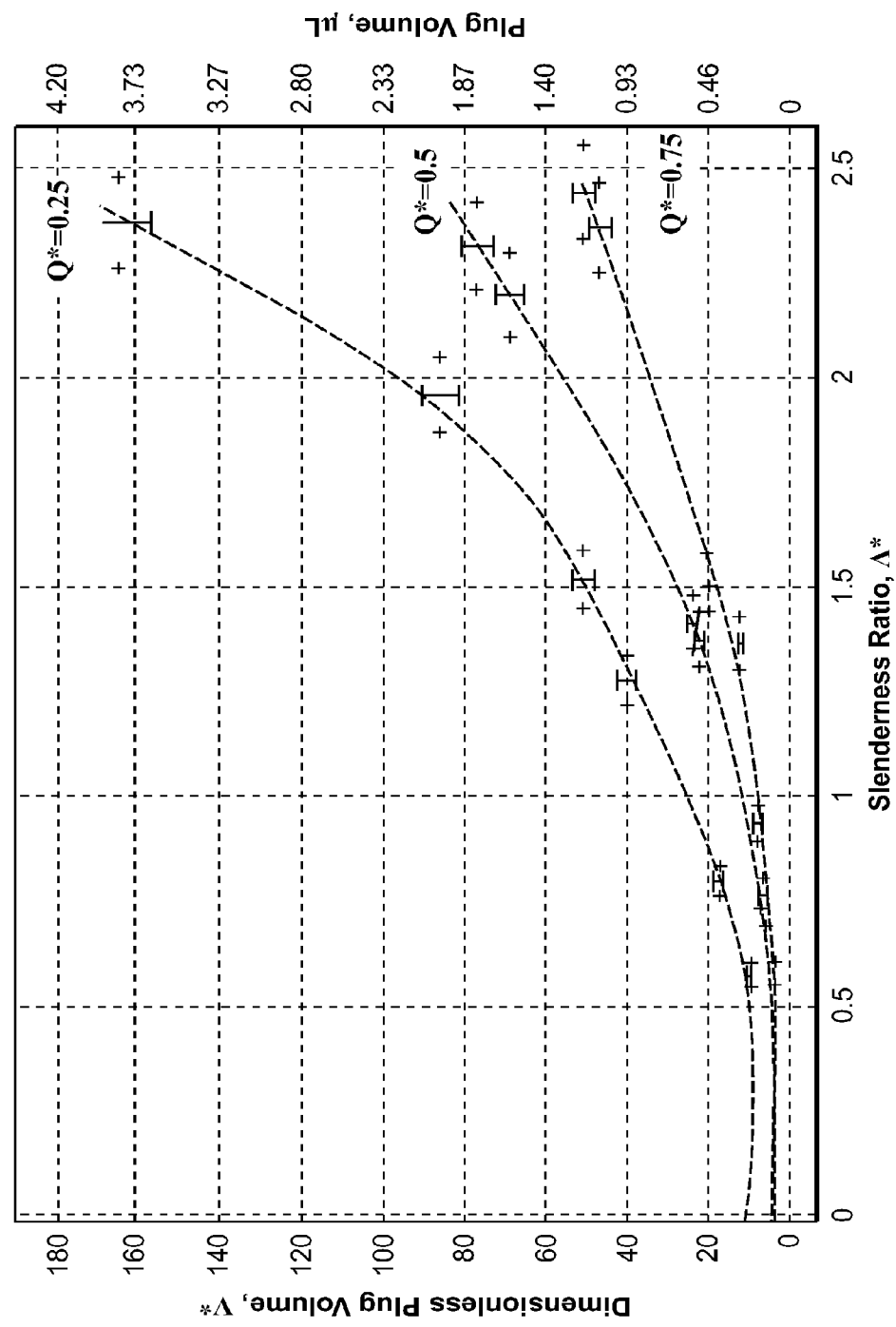
FIG. 7 is a characteristic plot for a liquid bridge segmentor.

The location of the stability boundary, or rupture point, was determined experimentally by fixing the slenderness, establishing a stable liquid bridge between capillary tips and withdrawing fluid from one capillary until rupture was observed. A digital image of the liquid bridge just prior to rupture was then analyzed, using an edge detection measurement technique to determine the total volume and hence the volumetric ratio, $V^*$. The slenderness was then adjusted and the experiment repeated. $K^*$ represents the ratio of the radius of the smaller disk, $R_1$, to the radius of the larger one, $R_2$, that is $K^*=R_1/R_2$. FIG. 7 shows the approximate location of the minimum volume stability boundary for liquid bridges with a lateral Bond number of $1.25\times10^{-4}$, a near weightless environment. Vertical and horizontal error bars indicate experimental uncertainty.

Figure 5:
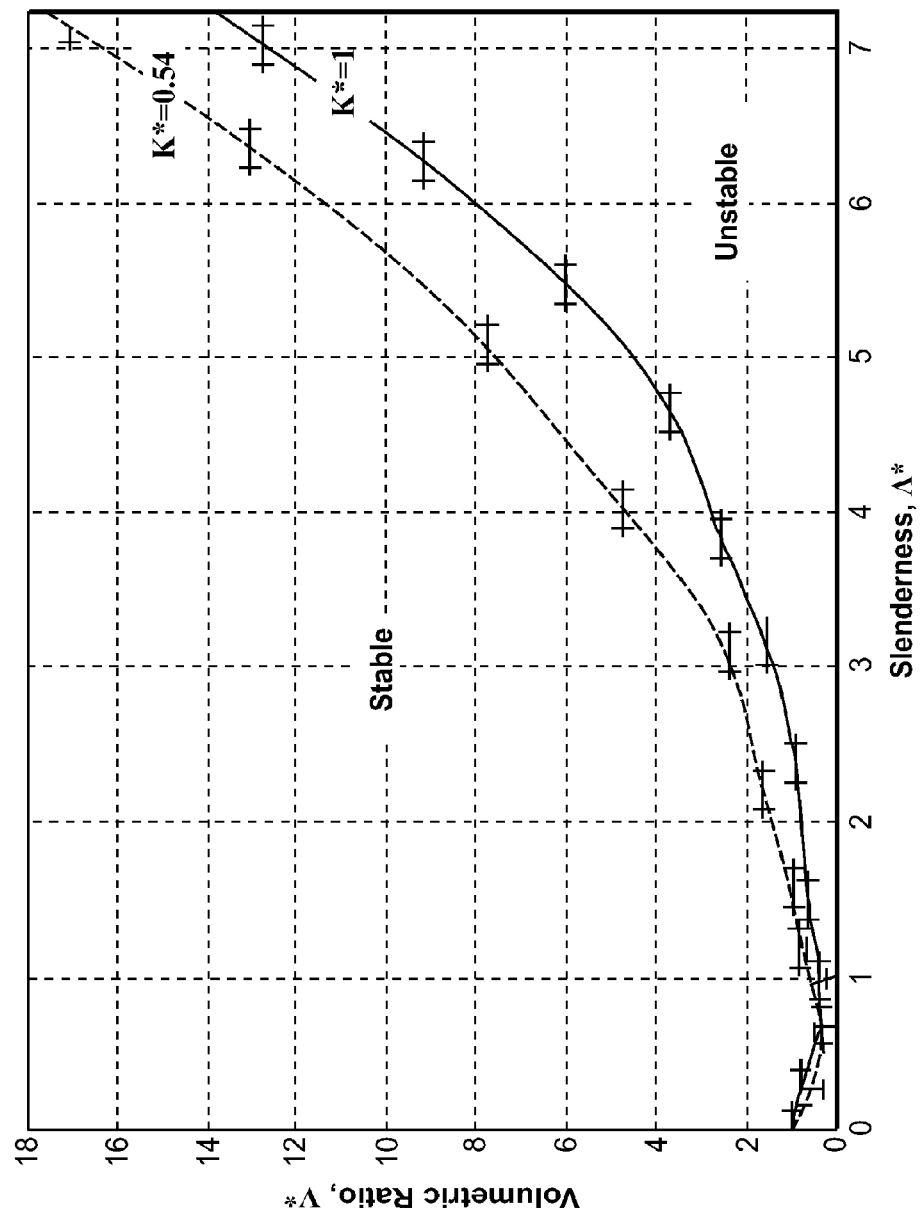
FIG. 5 is a diagram showing a characteristic plot of volumetric ratio vs. slenderness at a liquid bridge for segmentation.

At high volumetric ratios, FIG. 4 panel C for example, bridges maintain their integrity and reach a minimum energy configuration. At low volumetric ratios, FIG. 4 panel A for example, the bridges break before the interfacial energy is minimized. The initial dip in the stability boundary at low slenderness ratios was caused by low-volume droplets not fully wetting the exposed fused silica of the capillary tips. The influence of unequal capillaries on the $\Lambda^*-V^*$ stability diagram is also shown in FIG. 5. It can be seen that the unstable region of the $\Lambda^*-V^*$ plane increases as the parameter $K^*$, the ratio of capillary radii, decreases. The results presented in FIG. 5 confirmed that the static stability of liquid bridge is purely geometrical at low Bond numbers. It is notable that low slenderness ratio bridges are almost completely stable, with respect to rupture, for all capillary radii measured.

Rupture was observed only at very low volumetric ratios with the liquid bridge assuming a thimble shape. Liquid bridge instability when applied to fluid dispensing is particularly useful as a replacement for micro-channel shear-based dispensing systems. In more detail, FIG. 5 shows a stability diagram for a de-ionized water liquid bridge in a density matched silicone oil, Bond number: $1.25\times10^{-4}$. Vertical error bars indicate the volumetric ratio uncertainty as a result of camera frame rate. Horizontal error bars indicate slenderness uncertainty due to capillary tip misalignment. The parameter $K^*$ is the ratio of supporting capillary radii.

Example 3

Dispensing Sub-Microliter Volumes

The following describes the use of liquid bridge instability as a mechanism for dispensing sub-microliter volumes of fluid in a continuous manner. The dispensing mechanism provided a reliable means of producing uniform aqueous plugs separated by silicone oil that did not rely on the shear force exerted by the carrier fluid. The repeatability with which the method dispensed plugs was examined. The approach used the liquid bridge's dependence on geometry to create a periodic instability between opposing capillary tips. A stable liquid bridge was first established between aqueous inlet and outlet. The volume held in this bridge was then steadily reduced by the action of the silicone oil inlet. This caused the formation of an unstable liquid bridge that ruptured to release a smaller plug at the outlet. The segmenting mechanism provided a reliable means of producing uniform aqueous plugs separated by silicone oil that did not rely on the shear force exerted by the carrier fluid. Furthermore, a protective oil film was established between the walls of the circular capillaries and the droplet to prevent carryover contamination.

Figures 6A, 6B, 6C, 6D:
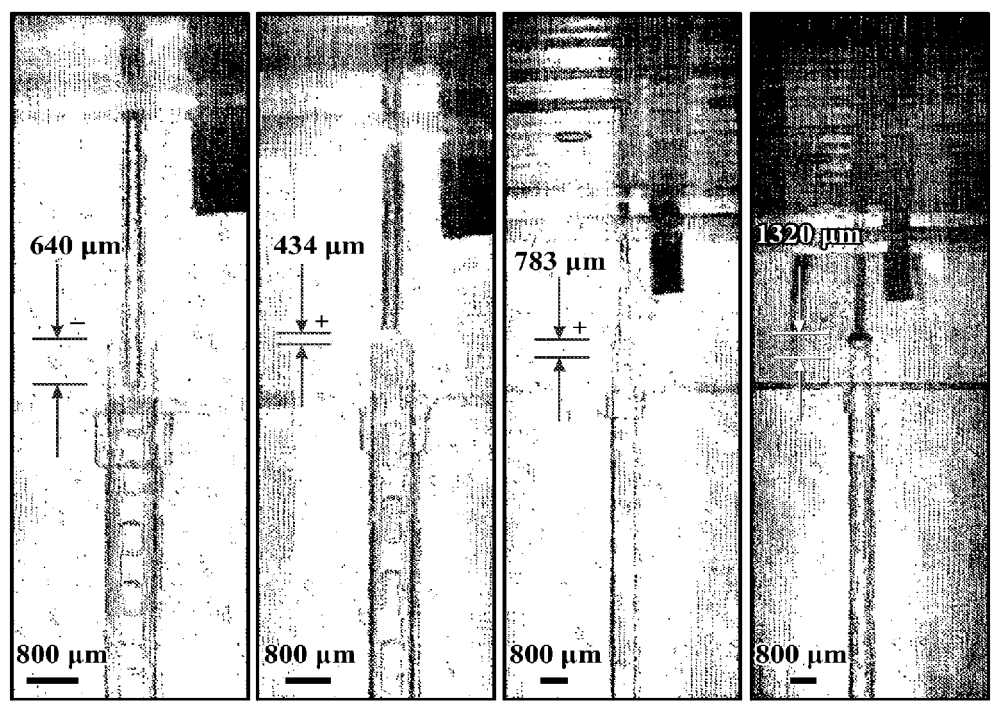
FIG. 6 is a set of photographs of liquid bridge segmentors having different geometries.

FIG. 6 panels A-D shows images of a liquid bridge dispensing at four different slenderness ratios. (A) $\Lambda^*=0$, (B) $\Lambda^*=0.76$, (C) $\Lambda^*=1.37$ and (D) $\Lambda^*=2.31$. $Q^*=0.5$, $K^*=0.44$. Increasing the capillary tip separation, and hence the slenderness ratio increased the plug volumes dispensed. $Q^*$, the oil flow rate as a fraction of the total flow rate, was maintained constant at 0.5. FIG. 6 panel A shows dispensing with the dispensing capillary inserted inside the outlet capillary. This configuration was assigned a slenderness ratio, $\Lambda^*$ of zero. Slenderness ratios close to zero resulted in the smallest volume plugs dispensed for this geometry. The effect of increasing tip separation on dispensed plug volume is shown in FIG. 6 panels B-D. Increasing tip separation, i.e. slenderness ratio, resulted in larger volume aqueous plugs punctuated by approximately the same volume of silicone oil. This was due to the silicone oil inlet flow rate being maintained constant and equal to the aqueous droplet inlet flow rate.

FIG. 7 presents a plot of $V^*$, against slenderness ratio, $\Lambda^*$, where $V^*$ is the dimensionless plug volume scaled with $R_0^3$, i.e.:

$$V^*=\overline{V}/R_0^3.$$

Results are presented for three different values of the oil flow rate fraction, $Q^*$, with the ratio of capillary tip radii, $K^*$, maintained constant at 0.44. The axis on the right-hand side of the plot indicates the measured plug volume. Horizontal error bars indicate slenderness uncertainty as a result of positional inaccuracy. Vertical error bar are a result of uncertainty in the plug volume calculation due to image processing. The results show the expected trend of increased plug volume with liquid bridge slenderness ratio. Decreasing $Q^*$ resulted in a dramatic increase in dimensionless plug volume. Altering $Q^*$ also affected the volume of silicone oil separating the aqueous plugs as $Q^*$ is the oil flow rate as a fraction of the total flow rate. The lowest repeatable volume measured using this particular geometry was approximately 90 mL with $\Lambda^*=0$, $Q^*=0.75$. The highest volume measured was approximately 3.9 µL with $\Lambda^*=2.36$, $Q^*=0.25$.

In flows where the non-wetting fluid, i.e. the aqueous phase, was displaced by wetting fluid, i.e. oil, a thin film of the wetting fluid separated the droplets from the capillary surface. The thickness of the film resulted from a balance between the oil viscosity, η, and the interfacial tension, $\sigma_i$. The thickness of the oil film deposited in a capillary of radius r is given by;

$$h = 1.34 r (Ca^{2/3}). \quad \text{(Equation (0.1))}$$

The capillary number, Ca, is given by:

$$Ca = \eta U / \sigma_i \quad \text{(Equation (0.2))}$$

where U represents the mean velocity of the flow. Equation (0.1) is obeyed if the film is thin enough to neglect geometric forces, h<0.1r, and thick enough to avoid the influence of long range molecular attraction, h>100 nm. Typical oil film thicknesses for plug flow through 400 μm polymeric fluorocarbon internal diameter tubing were calculated to be of the order of 1 μm.

This film thickness was too small to resolve with any degree of accuracy from experimental images. However, the oil film did form a protective coating preventing aqueous reactor fluid from contacting the Teflon tubing. This had the advantage of preventing a mechanism responsible for carry-over contamination whereby small droplets may be deposited onto the walls of micro-channels. Table 2 below presents two examples of oil-surfactant combinations that were used to successfully establish protective oil films around flowing droplets. Surfactant additives acted to change the interfacial tension between droplets and the oil carrier fluid such as to promote the establishment of a protective oil film, the thickness of which is given by Equation 0.1.

TABLE 2

| Oil | Surfactant | Concentration |
| --- | --- | --- |
| FC40 | 1H,1H,2H,2H-perfluoro-1-decanol | 2% W/V |
| AS100 Silicone Oil | Triton X-100 | 0.1% W/W in PCR Buffer Solution |

Figure 8:
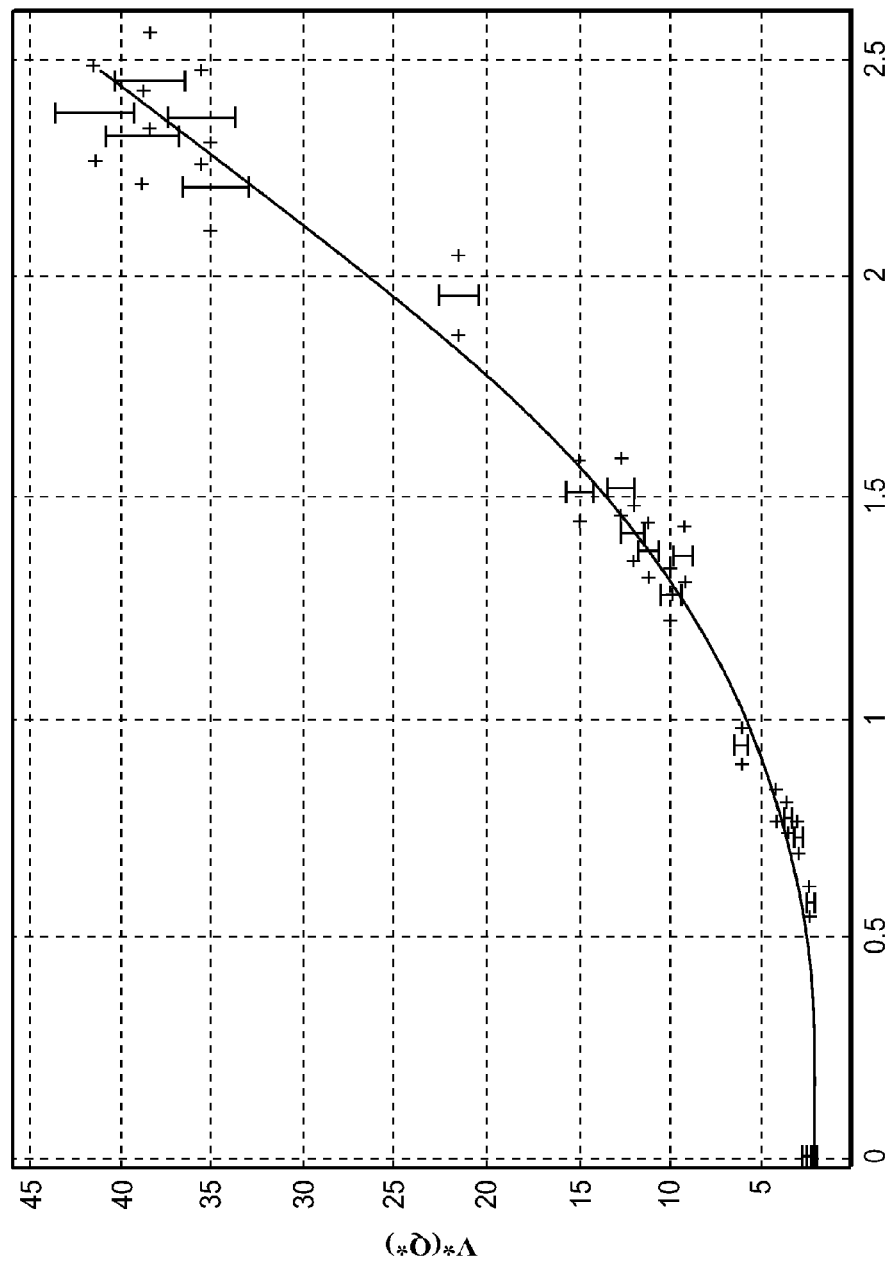
FIG. 8 is a collapsed data characteristic plot for liquid bridge segmentation.

FIG. 8 presents a dimensionless plot of the product of V* and Q* versus Λ*. The data, taken from the plot shown in FIG. 7, collapsed on to the trend line within the bounds of uncertainty. The data applied to geometries with K*=0.44. Notwithstanding this geometric constraint, the collapsed data did yield valuable design information.

Consider a microfluidic system designer deciding on an appropriate geometry for a segmenting device. The designer will usually know the exact volume to dispense from the outline specification for the device. If there is a sample frequency requirement, the designer may also know a value for Q*. Recalling that K*=$R_1/R_2$, where $R_1$ and $R_2$ are the inlet and outlet diameters respectively makes the design process relatively easy. Deciding on an arbitrary value for an outlet diameter fixes the aqueous inlet diameter as the data shown in FIG. 9 applies to only to geometries with K*=0.44. With this information in hand, an appropriate value for V*(Q*) may be calculated. The corresponding value for Λ* may then be read from the design curve shown in FIG. 8. Finally, Λ* was used to calculate the tip separation between the inlet and outlet.

Example 4

Droplet Volume with Respect to Liquid Bridges

Figure 10A:
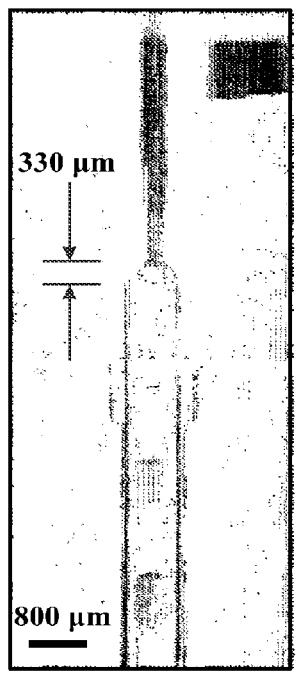
FIG. 10 is a set of photographs of three liquid bridge segmentors having different capillary radii.
Figure 10B:
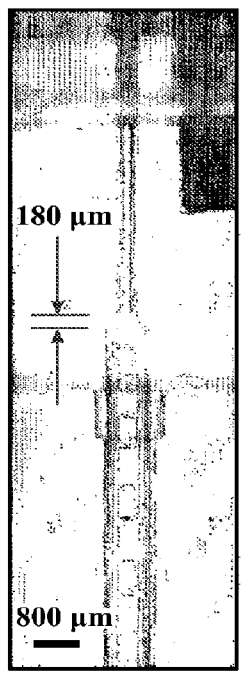
Figure 10C:
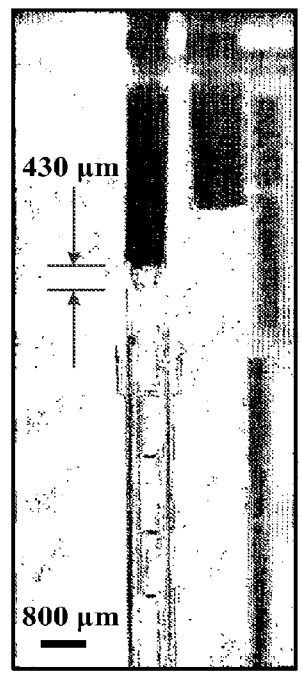

The data presented in FIGS. 7 and 8 applied to geometries with K*=0.44. The effect of altering K* on plug volumes dispensed was also investigated. FIG. 10 panels A-C shows a liquid bridge dispensing at three different values for K*. Panels (A), (B) and (C) correspond to K* values of 0.25, 0.44 and 1.0 respectively. K* value of 0.25 was achieved by assembling a 200 μm fused silica microcapillary at the end of a polymeric capillary tube by a reduction of internal diameter through appropriately sized fused silica. Sealing was ensured with the addition of cyanoacrylate glue at the sleeve interfaces.

Figure 9:
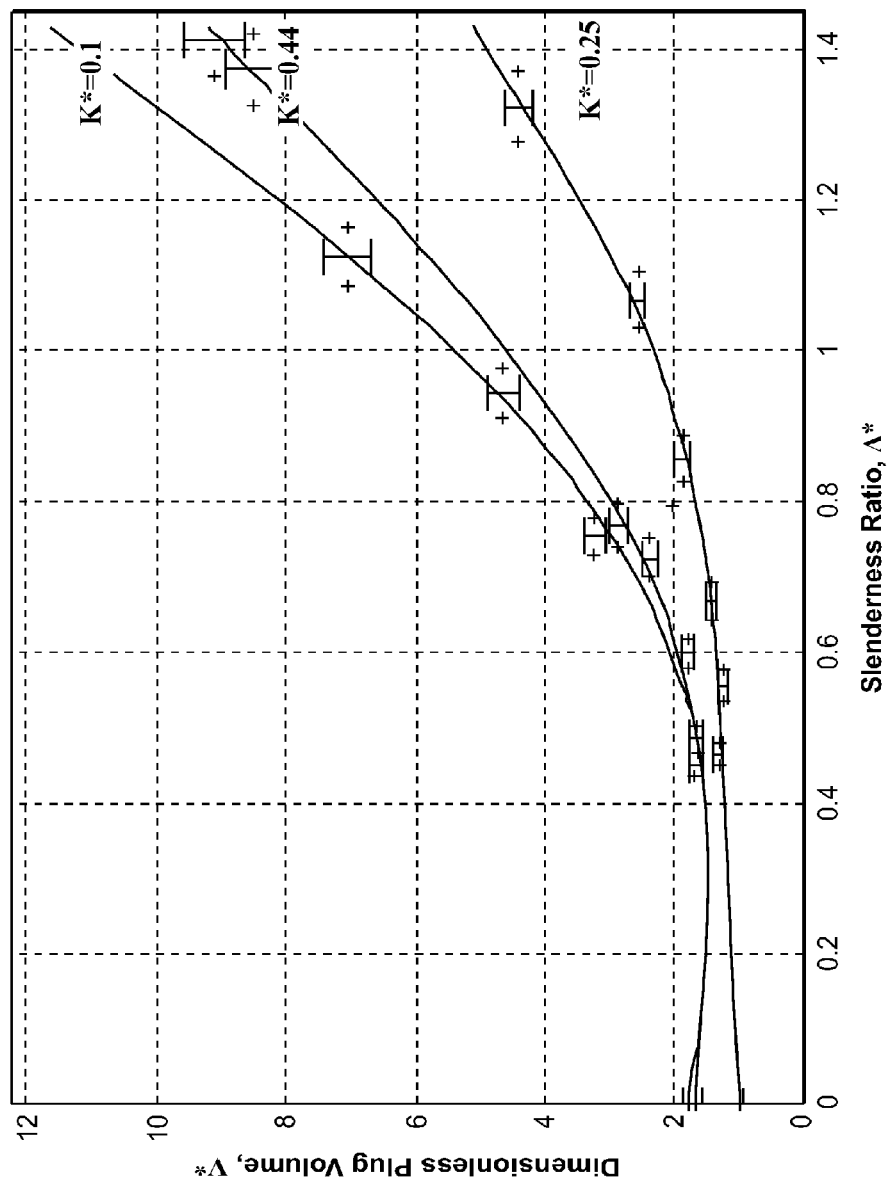
FIG. 9 is a further characteristic plot for a liquid bridge segmentor.

FIG. 9 presents a dimensionless plot of V* versus Λ* for three different values of K*. The dimensionless plug volume, V*, was scaled with $R_2^3$, and not $R_0^3$ as previously. This permitted a direct comparison of dimensionless plug volumes as $R_2$ remained constant throughout the experiment. It was observed that decreasing K* generally lowered the plug volumes dispensed for any given value of slenderness, Λ*. The minimum volume dispensed with K*=0.25 was approximately 60 nL whilst that of K*=0.44 and K*=1 was approximately 110 mL. Attempts to collapse the data shown in FIG. 9 onto a single line, similar to the plot shown in FIG. 8, were unsuccessful. This was due to the highly non-linear relationship between K* and V* for any given value of Λ*.

Example 5

Repeatability of Dispensing Sub-Microliter Volumes

Figure 11:
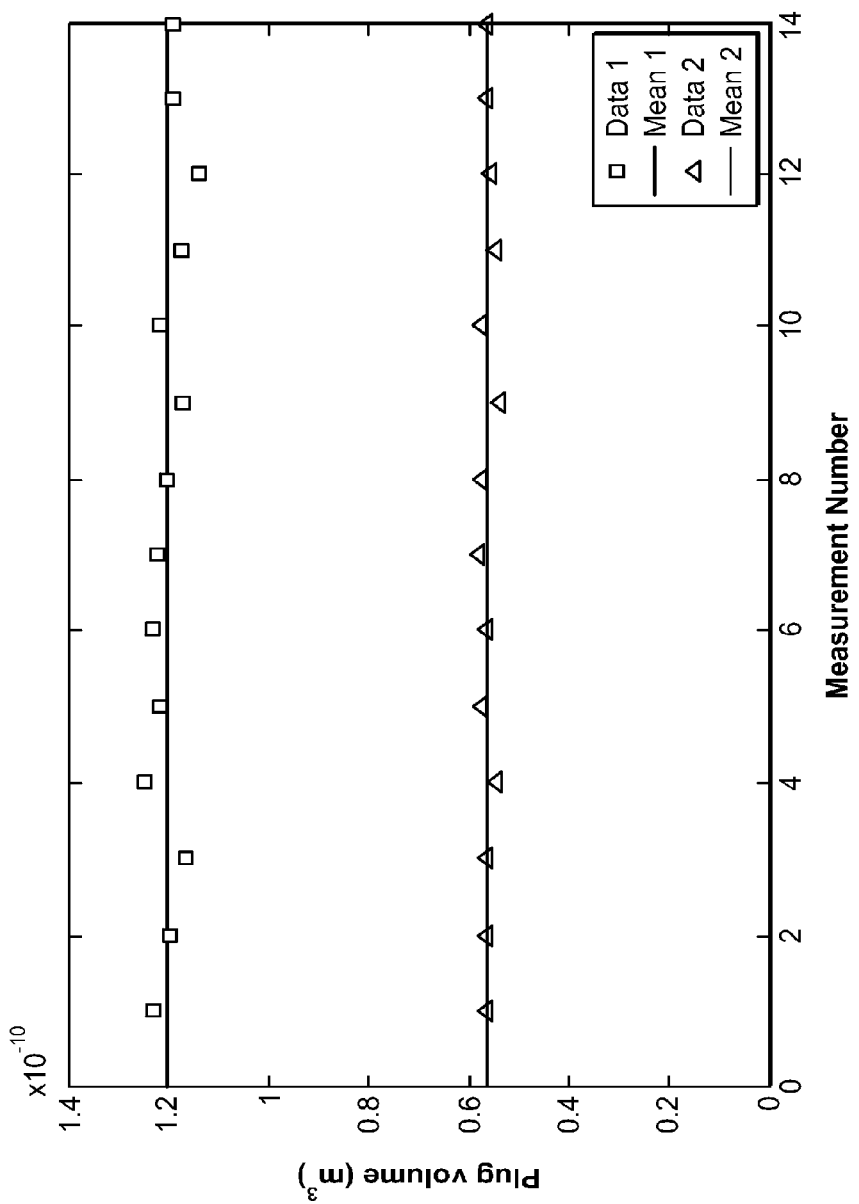
FIG. 11 is a further characteristic plot for a liquid bridge segmentor.

The repeatability with which the liquid bridge dispensing system could deliver fluid was of particular interest. FIG. 11 plots plug volume variation over fourteen measurements for a dispensing system with K*=0.44. The results show mean plug volumes of approximately 120 nL and 56 nL with maximum volumetric variations of ±4.46% and ±3.53% respectively. These volumetric variations compared favorably to commercial available micropipettes that have an uncertainty of ±12% when dispensing 200 nL. The accuracy with which one may dispense using micropipettes, however, is thought to be largely dependant upon user skill. The automation of dispensing systems may therefore be justified as a means of eliminating user-user variability. The volumetric analysis presented in FIG. 11 shows liquid bridge dispensing to be a very repeatable means of continuously dispensing sub-microliter volumes of fluid.

Figure 12:
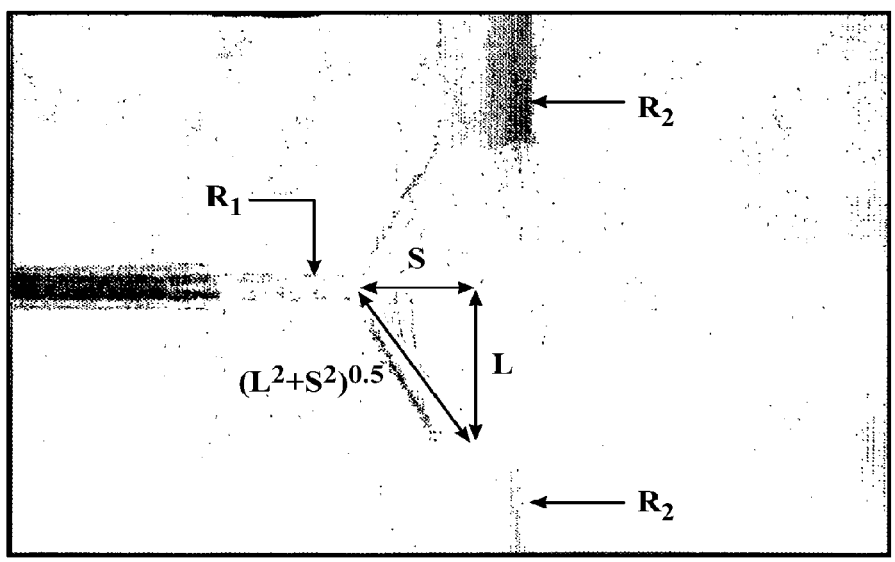
FIG. 12 is a photograph of a funicular bridge, also showing dimension parameters.

FIG. 12 is an image of a liquid bridge. The bridge consisted of two opposing capillaries of the same external diameter. The second inlet part was of a finer capillary orientated at right angles to and situated half-way between the other two capillaries. Constraints on opposing capillary radius and the placement of the third capillary helped to simplify the dimensionless stability study. The investigation also necessitated modifications to the dimensionless parameters characterizing axisymmetric liquid bridge geometry. The slenderness ratio, Λ*, was calculated using:

$$\Lambda^* = \frac{\sqrt{L^2 + S^2}}{2R_0}, \quad \text{Equation (1)}$$

where L and S correspond to the distances indicated in FIG. 12. $R_0$ is defined as the mean radius, i.e. $(R_1+R_2)/2$. K* is defined as $R_1/R_2$. The volumetric ratio, V*, is defined as:

$$V^* = \frac{V}{\pi R_0^2 \sqrt{L^2 + S^2}}, \quad \text{Equation (2)}$$

where ∇ is the measured volume at which bridge collapse occurs. In terms of the geometry presented in FIG. 12, a funicular bridge collapse corresponded to detachment from the finer capillary.

Figure 13:
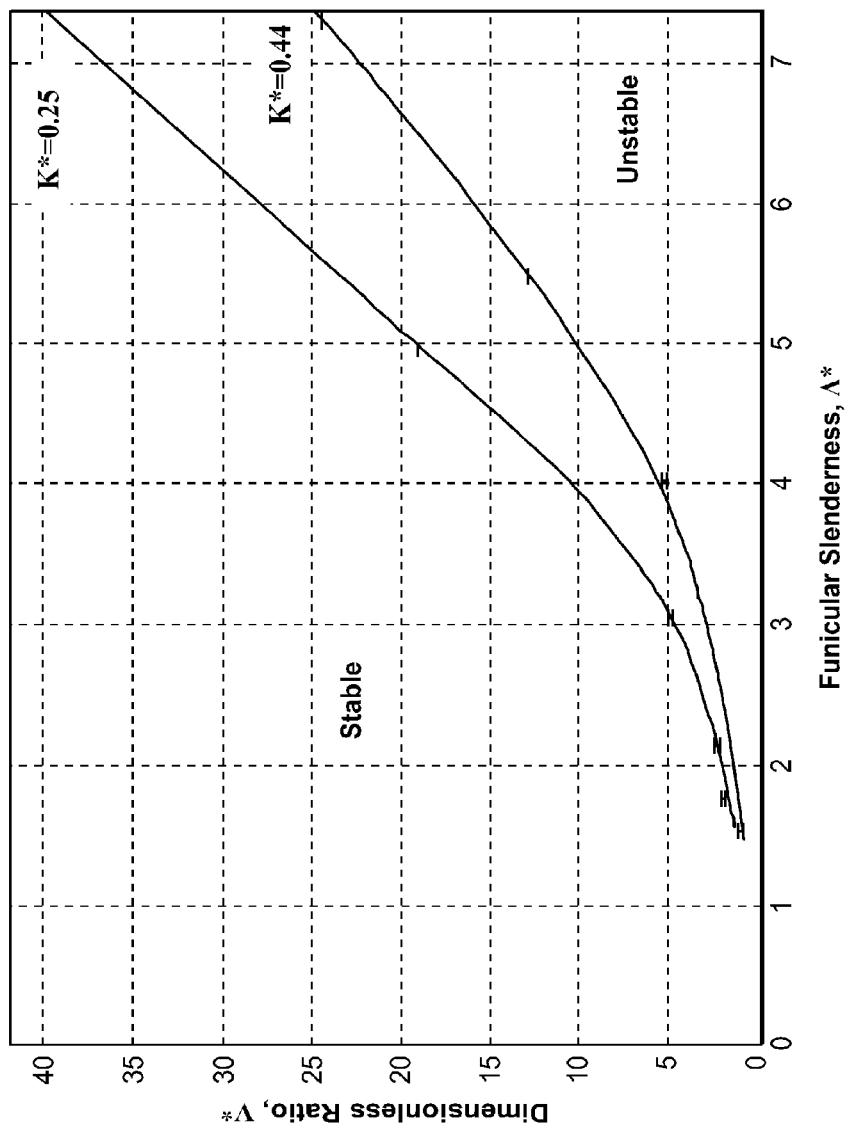
FIG. 13 is a funicular liquid bridge characteristic stability plot.

FIG. 13 shows a stability diagram for the approximate location of the minimum volume stability boundary for purified water funicular liquid bridges with a lateral Bond number of $1.25 \times 10^{-4}$, a near weightless environment. The boundaries of stability were found by fixing a value for $\Lambda^*$, establishing a stable funicular bridge and withdrawing fluid until the bridge collapsed. The collapse was recorded via a CCD and the frame immediately following rupture was analyzed to measure the volume. The calculation of the bridge volume was simplified by the fact that the collapsed funicular bridge exhibited axisymmetry with respect to the axis of the two larger capillaries. Minimum volume stability boundaries were plotted for $K^*=0.25$ and $K^*=0.44$. Lower $K^*$ values displayed increased instability. Volumetric data for $\Lambda^*$ values lower than approximately 1.5 were difficult to obtain with the geometry used and so were omitted from the stability diagram.

The formation of a funicular bridge deemed unstable by the graph shown in FIG. 13 ensured the injection of fluid into an aqueous plug passing through opposing capillaries. A further advantage to using funicular bridge dispensers is based on the speed at which the process takes place. Typical instabilities last of the order of 100 ms, insufficient time for the host droplet fluid to diffuse to the dispensing capillary tip. This is a further preventative measure against carryover contamination.

The two input one output, funicular bridge can be configured so that the expression profile of many genes may be addressed. One input contains the primer and premix in a continuous phase, the outlet then delivers them in droplet form. Firstly many input and output capillaries, say p, can be set in planes perpendicular to that of FIG. 1. A perpendicular arrangement allows for good optical access in the planar thermocycler which is connected to the output. Each arrangement of two inputs and one output can be used to address a single primer, giving p primers. This, however, would make for a very long device in the plane perpendicular to FIG. 1. If serially variant primers were fed into each input, numbering q, this would reduce the scale. Further, if the primers were multiplexed, to order r, in each droplet the scale would be further reduced. The number of primers that could then be addressed would be: $N = p \times q \times r$. By this means, a PCR test of the whole genome of any living form, including the human, could be addressed, which would have applications beyond diagnosis, in many fields of pure and applied science.

What is claimed is:

1. A method for analyzing an agricultural sample containing an analyte, the method comprising the steps of:
    providing an agricultural sample in a first fluid stream and a reagent in at least one reagent stream;
    mixing in a liquid bridge the sample with the at least one reagent stream to form a mixed droplet that is wrapped in an immiscible second fluid; and
    analyzing the mixed droplet to detect a trait of the agricultural sample.

2. The method according to claim 1, wherein the immiscible second fluid is oil.

3. The method according to claim 1, wherein the agricultural sample is selected from the group consisting of: a seed, a batch of seeds, a portion of a seed, or a seed scraping.

4. The method according to claim 1, wherein the agricultural sample comprises plant tissue.

5. The method according to claim 4, wherein the plant tissue is selected from the group consisting of: a leaf, a leaf punch, a flower, a root, and a petal.

6. The method according to claim 1, wherein the agricultural sample comprises non-plant based material.

7. The method according to claim 6, wherein the non-plant based material comprises a fungal sample.

8. The method according to claim 1, wherein the trait is a biochemical trait.

9. The method according to claim 8, wherein the biochemical trait is selected from the group consisting of: oil content, protein content, carbohydrate content, starch content, fiber content, water content, amino acid content, fatty acid content, nitrogen content, chlorophyll fluorescence, metabolites, oil composition, protein composition, carbohydrate composition, and fiber composition.

10. The method according to claim 1, wherein the desired trait is linked to a genetic marker.

11. The method according to claim 1, wherein the reagent is a labeled antibody specific for a gene or gene product of the agricultural sample.

12. The method according to claim 1, wherein the reagent is a labeled DNA probe or a labeled RNA probe.

13. The method according to claim 1, further comprising performing PCR on the gene in the mixed droplet.

14. The method according to claim 13, wherein the reagents comprise primers and polymerases.

15. A method for determining presence of a desired trait in a progeny agricultural sample comprising:
    obtaining a nucleic acid from a progeny agricultural sample, wherein the nucleic acid is in a first fluid;
    introducing the first fluid to a liquid bridge;
    introducing to the liquid bridge at least one reagent fluid;
    mixing at least a portion of the first fluid with the at least one reagent fluid to form a mixed droplet that is wrapped in an immiscible fluid;
    performing PCR on the nucleic acid in the mixed droplet; and
    analyzing the nucleic acid in the mixed droplet to determine presence of the desired trait in the progeny agricultural sample.

16. The method according to claim 15, wherein the immiscible second fluid is oil.

17. The method according to claim 15, wherein the agricultural sample is selected from the group consisting of: a seed, a batch of seeds, a portion of a seed, or a seed scraping.

18. The method according to claim 15, wherein the agricultural sample comprises plant tissue.

19. The method according to claim 18, wherein the plant tissue is selected from the group consisting of: a leaf, a leaf punch, a flower, a root, and a petal.

20. The method according to claim 15, wherein the desired trait is a genetically inheritable trait.

21. The method according to claim 20, wherein the genetically inheritable trait is selected from the group consisting of: pod color, flower color, seed yield, pubescence color, and herbicide resistance.

22. The method according to claim 15, wherein the reagents comprise primers and polymerases.

23. A method for analyzing an environmental sample for presence of a biological agent comprising:
    providing a liquid bridge for combining and mixing an aliquot of an environmental sample in a first fluid with at least one reagent in a second fluid to form a mixed droplet that is wrapped in an immiscible fluid;

combining and mixing the aliquot in the first fluid with the at least one reagent in the second fluid to form the mixed droplet that is wrapped in the immiscible fluid; and analyzing the mixed droplet to detect presence or absence of a biological agent in the environmental sample.

24. The method according to claim 23, wherein the immiscible second fluid is oil.

25. The method according to claim 23, wherein the biological agent is selected from the group consisting of: a toxin, an allergen, a metabolite, a bacteria, a yeast, a mold, and a fungus.

26. The method according to claim 23, wherein the environmental sample is a soil sample or a water sample.

27. The method according to claim 23, wherein the reagent is a labeled antibody specific for the biological agent in the environmental sample.

28. The method according to claim 23, wherein the reagent is a labeled DNA probe or a labeled RNA probe.

29. The method according to claim 23, wherein prior to the providing step, the method further comprises obtaining a gene or gene product from the biological agent in the environmental sample.

30. The method according to claim 29, wherein the reagent is a labeled antibody specific for the gene or gene product from the biological agent in the environmental sample.

31. The method according to claim 29, wherein the reagent is a labeled DNA probe or a labeled RNA probe that binds to the gene or gene product from the biological agent in the environmental sample.

32. The method according to claim 29, wherein prior to the analyzing step, the method further comprises performing PCR on the gene from the biological agent in the mixed droplet.

33. The method according to claim 32, wherein the reagents comprise primers and polymerases.

* * * * *

UNITED STATES PATENT AND TRADEMARK OFFICE
CERTIFICATE OF CORRECTION

PATENT NO. : 8,735,169 B2
APPLICATION NO. : 12/469339
DATED : May 27, 2014
INVENTOR(S) : Mark Davies and Tara Dalton It is certified that error appears in the above-identified patent and that said Letters Patent is hereby corrected as shown below:

CLAIMS:

Claim 14, col. 18, line 28. please delete "reagents comprise" and insert --at least one reagent stream comprises--

Claim 16, col. 18, line 45. please delete "second" fluid is oil.

Claim 22, col. 18, line 61. please delete "reagents comprise" and insert --at least one reagent fluid comprises--

Claim 24, col. 19, line 7. please delete "second" fluid is oil.

Claim 27, col. 19, line 14. insert --at least one-- reagent is a labeled antibody specific for the biological agent in the environmental sample.

Claim 28, col. 19, line 17. insert --at least one-- reagent is a labeled DNA probe or a labeled RNA probe.

Claim 30, col. 20, line 5. insert --at least one-- reagent is a labeled antibody specific for the gene or gene product from the biological agent in the environmental sample.

Claim 31, col. 20, line 8. insert --at least one-- reagent is a labeled DNA probe or a labeled RNA probe that binds to the gene or gene product from the biological agent in the environmental sample.

Claim 33, col. 20, line 17. delete "reagents comprise" and insert --at least one reagent comprises-- primers and polymerases.

Signed and Sealed this
Twenty-ninth Day of March, 2016

Michelle K. Lee
*Director of the United States Patent and Trademark Office*